US009265559B2

(12) United States Patent
Godara et al.

(10) Patent No.: US 9,265,559 B2
(45) Date of Patent: Feb. 23, 2016

(54) ELECTROSURGICAL METHOD

(75) Inventors: Neil Godara, Milton (CA); Taylor Hillier, Georgetown (CA); Matthew Parker, Deep River (CA); Hua Xin Lo, Toronto (CA); Jason Woo, Vaughan (CA)

(73) Assignee: Avent, Inc., Alpharetta, GA (US)

( * ) Notice: Subject to any disclaimer, the term of this patent is extended or adjusted under 35 U.S.C. 154(b) by 1222 days.

(21) Appl. No.: 12/036,605

(22) Filed: Feb. 25, 2008

(65) Prior Publication Data

US 2008/0228181 A1 Sep. 18, 2008

Related U.S. Application Data

(60) Provisional application No. 60/891,523, filed on Feb. 25, 2007.

(51) Int. Cl.
*A61B 18/12* (2006.01)
*A61B 18/00* (2006.01)

(52) U.S. Cl.
CPC ... *A61B 18/1206* (2013.01); *A61B 2018/00702* (2013.01); *A61B 2018/00791* (2013.01)

(58) Field of Classification Search
CPC ...... A61B 18/04; A61B 18/042; A61B 18/08; A61B 18/082; A61B 18/10; A61B 18/12; A61B 18/1206; A61B 18/1233; A61B 18/14; A61B 18/148; A61B 18/1402; A61B 18/148; A61B 18/1842; A61B 18/1485; A61B 2018/00577; A61B 2018/00589; A61B 2018/00595; A61B 2018/00601; A61B 2018/00607; A61B 2018/00642; A61B 2018/00648; A61B 2018/00702; A61B 2018/00714; A61B 2018/00779; A61B 2018/00791; A61B 2018/00815; A61B 2018/00898; A61B 2018/0212; A61B 2018/1816
USPC ....................................... 606/32–35; 198/898
See application file for complete search history.

(56) References Cited

U.S. PATENT DOCUMENTS

| 4,727,874 | A | 3/1988 | Bowers et al. | |
|---|---|---|---|---|
| 5,817,093 | A | 10/1998 | Williamson, IV et al. | |
| 6,183,468 | B1 * | 2/2001 | Swanson et al. | 606/40 |
| 6,228,081 | B1 | 5/2001 | Goble | |
| 6,537,272 | B2 * | 3/2003 | Christopherson et al. | 606/34 |
| 6,730,080 | B2 * | 5/2004 | Harano et al. | 606/38 |
| 7,258,688 | B1 | 8/2007 | Shah et al. | |
| 7,344,532 | B2 | 3/2008 | Goble et al. | |
| 7,678,105 | B2 | 3/2010 | McGreevy et al. | |
| 7,699,842 | B2 | 4/2010 | Buysse et al. | |
| 7,722,601 | B2 | 5/2010 | Wham et al. | |
| 7,901,400 | B2 | 3/2011 | Wham et al. | |
| 2001/0020166 | A1 * | 9/2001 | Daly et al. | 606/34 |
| 2001/0029369 | A1 * | 10/2001 | Kannenberg et al. | 606/34 |
| 2002/0058933 | A1 * | 5/2002 | Christopherson et al. | 606/34 |
| 2003/0073989 | A1 * | 4/2003 | Hoey et al. | 606/34 |
| 2004/0077934 | A1 | 4/2004 | Massad | |
| 2005/0010206 | A1 * | 1/2005 | Nasab et al. | 606/41 |

* cited by examiner

*Primary Examiner* — Michael Peffley
*Assistant Examiner* — Khadeijeh Vahdat
(74) *Attorney, Agent, or Firm* — Dority & Manning, P.A.

(57) ABSTRACT

Methods are disclosed for delivering energy to a body of a human or animal during a treatment procedure using an electrosurgical generator, a pre-set overall procedure time being defined for the treatment procedure, a ramp time being defined for a parameter to reach a pre-set threshold during the treatment procedure, the method comprising: measuring the parameter over time; and if the parameter has not substantially reached the pre-set threshold by the ramp time, setting a procedure extension time responsive to the time difference between the ramp time and the time at which the pre-set threshold was reached, and extending the overall procedure time by the procedure extension time.

6 Claims, 4 Drawing Sheets

ELECTROSURGICAL METHOD

CROSS-REFERENCES TO RELATED APPLICATIONS

This application claims the benefit of U.S. Provisional Patent Application Ser. No. 60/891,523, filed on Feb. 25, 2007, which is hereby incorporated by reference in its entirety.

TECHNICAL FIELD

The invention relates to methods for electrosurgical procedures and systems that may employ such methods. More particularly, it relates to systems and methods operable to vary one or more treatment parameters intra-procedurally.

BACKGROUND OF THE ART

Typical electrosurgical procedures involve the delivery of energy for a pre-set period of time in order to effect a desired treatment within a patient's body. Oftentimes, the procedure will require that the temperature of the tissue being treated be raised to a pre-set threshold by the delivery of energy within a pre-set time frame and be maintained at that threshold for a period of time in order to effect the desired treatment. In some such procedures, the temperature may not reach the pre-set threshold within the pre-set time frame and may therefore not be maintained at the threshold for a sufficient time in order to effect the desired treatment, since the overall procedure time is pre-set and is not modified during the procedure. Typical prior art electrosurgical systems are not operable to compensate intra-procedurally for such a situation. Alternatively, other prior art systems do not define a pre-set overall procedure time and rather start the treatment time counter once the threshold temperature has been reached. In such cases, the user is left guessing as to how long the overall procedure will be, as it would depend on when the threshold temperature is reached. The present invention, therefore, seeks to overcome these limitations of the prior art.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
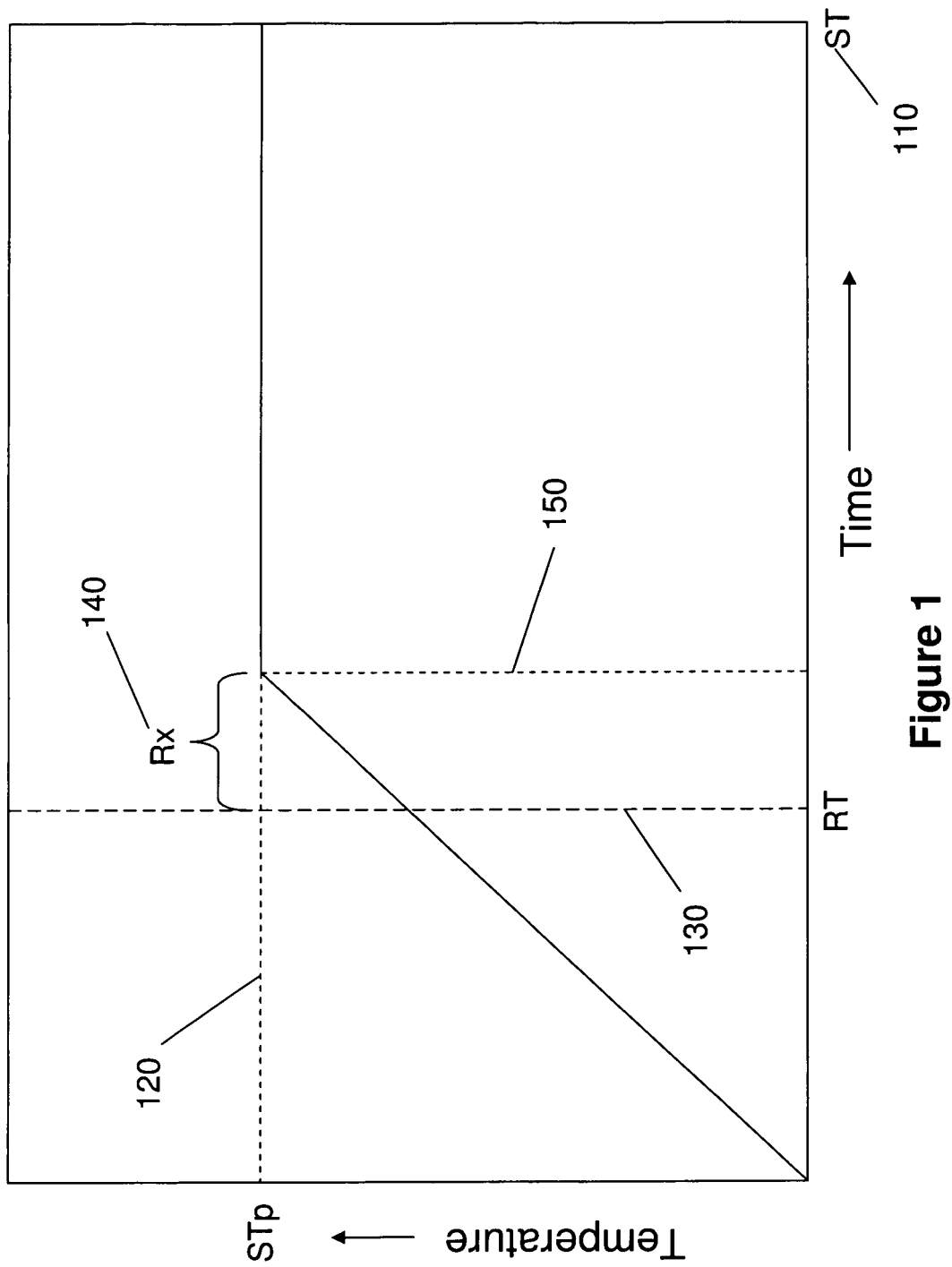
FIG. 1 is a graph showing a plot of temperature vs. time for an embodiment of the present invention.

In one broad aspect, embodiments of the present invention comprise a method for delivering energy to a body of a human or animal during a treatment procedure using an electrosurgical generator, a pre-set overall procedure time being defined for the treatment procedure, a ramp time being defined for a parameter to reach a pre-set threshold during the treatment procedure, the method comprising: measuring the parameter over time; and if the parameter has not substantially reached the pre-set threshold by the ramp time, setting a procedure extension time responsive to the time difference between the ramp time and the time at which the pre-set threshold was reached, and extending the overall procedure time by the procedure extension time.

In another broad aspect, embodiments of the present invention comprise a computer readable medium including computer-executable instructions for interfacing with an electrosurgical generator during a treatment procedure, a pre-set overall procedure time being defined for the treatment procedure, a ramp time being defined for a parameter to reach a pre-set threshold during the treatment procedure, the computer-executable instructions performing a method comprising: measuring the parameter over time; and if the parameter has not substantially reached the pre-set threshold by the ramp time, setting a procedure extension time responsive to the time difference between the ramp time and the time at which the pre-set threshold was reached, and extending the overall procedure time by the procedure extension time.

As a feature of this aspect, the computer readable medium includes, but is not limited to, a floppy disk, a hard disk, a CD/DVD ROM, a flash memory device, and non-volatile ROM and RAM.

In an additional broad aspect, embodiments of the present invention comprise an electrosurgical system comprising an electrosurgical generator for delivering energy to a body of a human or animal during a treatment procedure, a pre-set overall procedure time being defined for the treatment procedure, a ramp time being defined for a parameter to reach a preset threshold during the treatment procedure, the electrosurgical system being operable to: measure the parameter over time; and, if the parameter has not substantially reached the pre-set threshold by the ramp time, set a procedure extension time responsive to the time difference between the romp time and the time at which the pre-set threshold was reached, and extend the overall procedure time by the procedure extension time.

In a further broad aspect, embodiments of the present invention comprise an electrosurgical system comprising an electrosurgical generator for delivering energy to a body of a human or animal during a treatment procedure, a pre-set overall procedure time being defined for the treatment procedure, a ramp time being defined for a parameter to reach a pre-set threshold during the treatment procedure, the electrosurgical system being operable to: measure the parameter at one or more times during the treatment procedure; and, if the parameter has not substantially reached the pre-set threshold by the ramp time, set a procedure extension time responsive to the time difference between the ramp time and the time at which the pre-set threshold was reached, and extend the overall procedure time by the procedure extension time.

As a feature of this aspect, the parameter is measured, for example, at the initiation of the treatment procedure as well as at the ramp time. In alternate embodiments, the parameter is measured, for example, at or near the ramp time and/or at or near the time corresponding to the romp time plus a maximum procedure extension time.

In yet a further broad aspect, embodiments of the present invention comprise a method for intra-procedurally assessing a likelihood of failure of a treatment procedure, the treatment procedure comprising delivering energy to a body of a human or animal using an electrosurgical generator, a treatment parameter being associated with the treatment procedure, the treatment parameter having a pre-set threshold associated with a successful treatment procedure, and a different parameter being associated with the treatment procedure, the different parameter having a pre-set limit, the method comprising: measuring the treatment parameter over time; and, during the course of the treatment procedure, determining whether or not the treatment parameter will reach the pre-set threshold such that the treatment procedure is likely to be successful, by correlating the measured treatment parameter with the different parameter; whereby the procedure is likely to fail if the treatment parameter does not reach the pre-set threshold prior to the different parameter reaching the pre-set limit.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Embodiments of the present invention are used in conjunction with a treatment procedure involving the delivery of energy to a patient's body. In order to appreciate the present invention in context, a typical electrosurgical procedure will be presently described.

A typical electrosurgical procedure comprises the following steps: energy is delivered to a patient from an energy source through at least one energy delivery device; a parameter is measured which is indicative of a temperature in the vicinity of the at least one energy delivery device; the measured parameter is assessed, and, if the assessment determines that the parameter measurement is unacceptable, at least one energy delivery parameter is modified.

Delivering energy may involve delivering energy through the at least one energy delivery device in any of a variety of configurations, for example, in a monopolar configuration, whereby energy may be delivered via one or more energy delivery devices through a patient's body to a separate return electrode, or in a bipolar configuration, whereby energy flows substantially between two or more energy delivery devices. If two or more energy delivery devices are used in a bipolar configuration, any device may be an active or return electrode. In further embodiments, energy delivery devices may be configured in a multipolar or multiphasic arrangement, whereby the energy delivery devices are configured such that the electrical potential and/or the phase of energy transmitted to at least two of the energy delivery devices differs in such a way to cause energy to flow in a desired direction between the energy delivery devices. The at least one energy delivery device is electrically coupled to an electrosurgical generator, whereby the generator as well as the at least one energy delivery device are understood to be components of an electrosurgical system. The energy delivered by the generator to the energy delivery device(s) may be high-frequency electromagnetic energy (such as radiofrequency (RF) energy).

Depending on the voltage provided to the patient, the energy may generate sufficient heat in the tissue to cause lesions due to ablation or coagulation. In the context of the present invention, 'ablation' refers to raising the temperature of a tissue such that at least a portion of the tissue is coagulated and a lesion is formed within the tissue. In other embodiments, tissue may be vaporized, creating a gap or hole in a tissue.

The characteristics of the energy being delivered (for example, the voltage, power, current, or frequency) may change throughout a course of a treatment procedure and may vary based on one or more of, but not limited to, user input, characteristics of any element of a system being used an association with the method of the invention, a calculated or measured parameter, or total treatment time elapsed.

During the course of a typical treatment procedure, a parameter indicative of a temperature in the vicinity of the energy delivery device is often measured. This measurement may involve measuring the temperature of the energy delivery device itself, if said temperature is indicative of the temperature of the tissue in which it is placed. In other cases, the temperature of the tissue may be inferred by some other means, or may be measured directly, for example, using a probe that extends from the surface of an energy delivery device, or by using a temperature sensor that independently contacts the tissue.

The assessment of the measured parameter may include, but is not limited to, one or more of: the direct comparison of one or more temperature measurements with one or more expected or pre-determined parameters (for example, accepting any temperature below a preset upper limit of 80° C., or above a preset lower limit of 60° C.); comparing a measured parameter to a previously measured parameter (for example, rejecting any temperature that is >20° C. above the previous measurement for the same device); averaging or otherwise comparing one or more expected parameters (for example, accepting any temperature that is within 5° C. of an average temperature and/or within 25° C. of other measured temperatures); analyzing one or more measured parameters, for example using a PID algorithm; or comparison of a measured parameter to another treatment parameter such as such as total treatment time elapsed, known tissue characteristics, patient history, or characteristics of the energy being delivered. The assessment of the measured parameter may optionally comprise the generation of one or more calculated parameters (for example, an average temperature value).

If the assessment of the measured parameter results in the rejection of one or more of the measurements, one or more parameters of energy delivery may be modified. For example, if a temperature is found to be too low, the following may occur: the energy delivered by the generator to the energy delivery device may be increased, the time during which energy is delivered to the energy delivery device may be increased, or a combination of the two. Alternatively, if the temperature is found to be too high, one or more of the following may occur: the energy delivered by the generator to the energy delivery device may be decreased, the time during which energy is delivered to the energy delivery device may be decreased, or the delivery of energy may be substantially stopped.

As will described in greater detail below, and in conjunction with embodiments of the present invention, after assessment of the measured parameter and modification of at least one energy delivery parameter, if necessary, a further assessment is made whether to continue energy delivery or to terminate the procedure. In some embodiments, this further assessment may be made at any point during the procedure, and may occur more than once during a given time period. This assessment may be based on, for example, user input, total treatment time elapsed, one or more measured or calculated parameters, or on the satisfaction of one or more error conditions inherent to the system. Termination of the procedure need not necessarily entail the cessation of energy delivery and may instead involve switching to a different mode, procedure, or algorithm.

With reference now to FIG. 1, and in accordance with the first broad aspect of the present invention, some embodiments provide a method of adjusting one parameter of a treatment procedure in response to a measured parameter associated with the treatment procedure. For example, in some embodiments, the treatment procedure defines various parameters for energy delivery, including but not limited to: an overall procedure time 110 (ST), a pre-set parameter threshold or limit, for example a set temperature (STp) 120, and a ramp time (RT) 130 for a parameter to reach the pre-set threshold or limit.

In some embodiments, a measured parameter, for example the temperature associated with an energy delivery device as described hereinabove, may not reach the pre-set threshold or limit, for example the set temperature 120, within the allotted ramp time 130. This may occur, for example, when a plurality of energy delivery devices are used, such that the energy provided to any given energy delivery device may be less than that required to substantially raise the temperature to the set temperature 120 by the pre-set ramp time 130. Alternatively, in embodiments comprising a single energy delivery device, the power output of the generator may be otherwise limited or the initial set temperature 120 may be sufficiently high such that it is not reached by the pre-set ramp time 130.

Figure 2A:
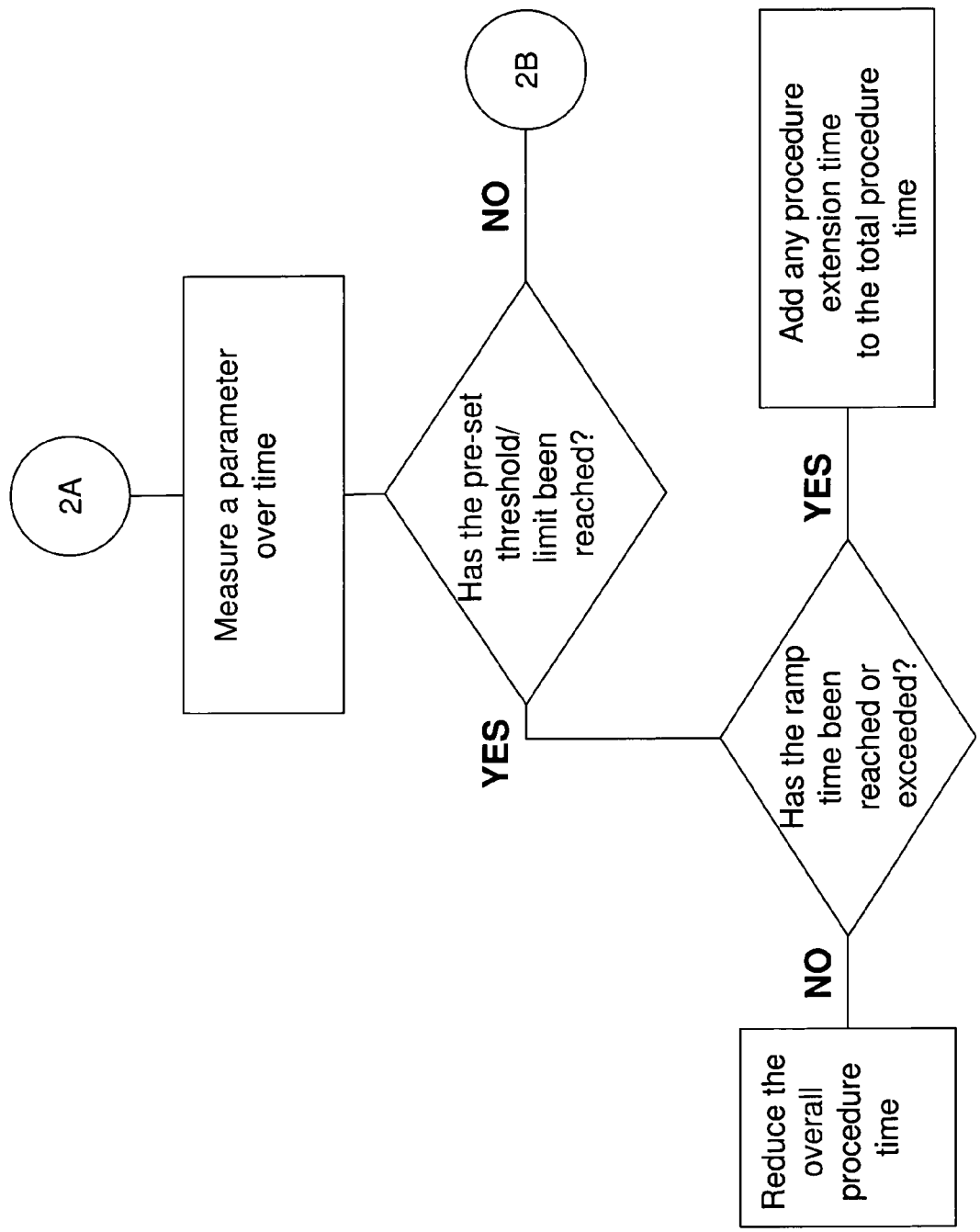
FIGS. 2A-2B are flow charts illustrating several aspects of embodiments of the present invention.

In such embodiments, a method of the present invention further comprises: measuring a parameter, for example the temperature associated with one or more energy delivery devices, over time; if the parameter has not reached the pre-set threshold or limit, for example the set temperature 120, substantially by the ramp time 130 then, when the parameter reaches the pre-set threshold or limit, for example the set temperature 120, setting a procedure extension time (Rx) 140, responsive to the time difference between the ramp time 130 and the time 150 at which the pre-set threshold or limit was reached; and extending the overall procedure time 110 by the procedure extension time 140. An exemplary embodiment of this method is illustrated in FIG. 2A.

For clarification, a particular example of such an embodiment will be presently described. This example is provided as a specific application of an embodiment of the present invention, and is not intended to limit the invention. In some procedures, it is beneficial for a specified parameter, for example the temperature associated with one or more energy delivery devices, to have a certain value, for example a set temperature, for a given amount of time. For example, a treatment procedure may have an overall procedure time of about 2 minutes and 20 seconds (2:20). It may be desirable, in such a procedure, for the temperature associated with one or more of the energy delivery devices to be maintained at about 60° C. for a period of about 2 minutes in order to effectively treat a portion of the patient's body, with a pre-set ramp time of about 20 seconds. If the temperature reaches 60° C. after 30 seconds, then the total time for which the temperature will be at 60° C. is about 1 minute and 50 seconds (i.e. overall procedure time [2:20] minus the time taken to reach the set temperature [0:30]=1:50), which is less than the desired 2 minutes. In such instances, it would be beneficial to adjust the overall procedure time to account for any delays in reaching the desired parameter value. Embodiments of the present invention therefore adjust the overall procedure time by a time responsive to, and in some cases substantially equivalent to, the delay between the pre-set romp time (in this example, 0:20) and the time actually taken to reach the parameter limit (in this example, 0:30). In the present example, this procedure extension time would be 10 seconds, which would be added to the overall procedure time in order to allow for the temperature to be at 60° C. for the full two minutes.

Figure 3:
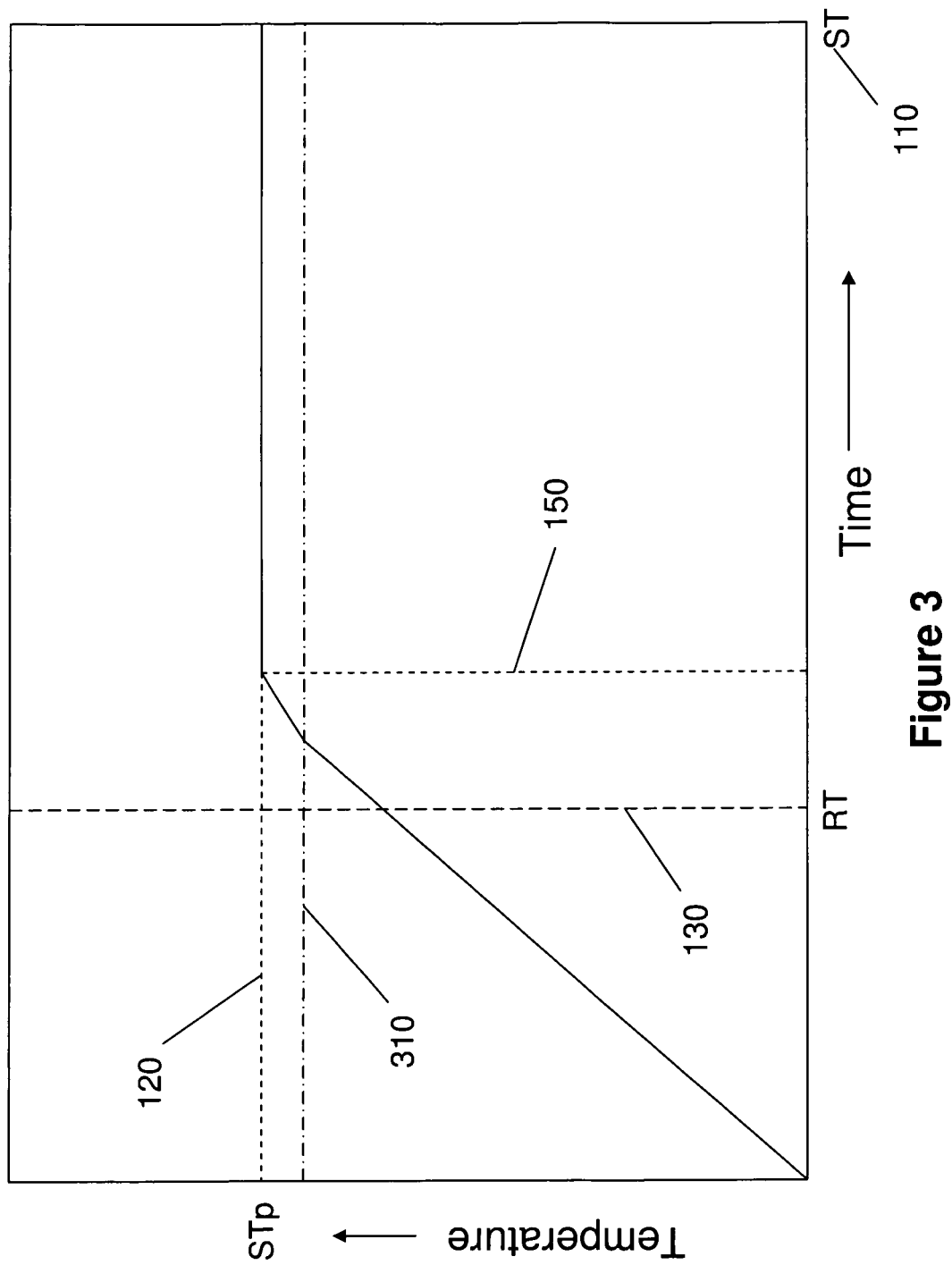
FIG. 3 is a graph showing a plot of temperature vs. time for an alternate embodiment of the present invention.

In alternate embodiments, for example if the measured temperature is sufficiently close to the set temperature for a period of time prior to reaching the set temperature, the procedure extension time may be responsive to but substantially less than the difference between the ramp time and the time at which the set temperature was reached. For example, if the temperature is measured to be about 59° C. for about 5 seconds prior to reaching the set temperature in the example described above, then the procedure extension time may be set to about 7.5 seconds, rather than the full 10 seconds, since the temperature in the 5 seconds immediately preceding the time at which the set temperature was reached was sufficiently close to the set temperature. Thus, such embodiments of the present invention may utilize pre-set tolerance levels to calculate the amount of time by which the procedure should be extended. In the example described hereinabove, the tolerance level may be, for example, about 1° C. to about 3° C., such that if the measured temperature is within about 1° C. to about 3° C. of the set temperature for a certain period of time after the ramp time, then the procedure extension time may be a pre-set fraction, for example between about 25% and about 75%, of the time difference between the time that the tolerance level was reached and the time at which the set temperature was reached. An example of such an embodiment is shown in FIG. 3, where the threshold level 310 is reached about 5 seconds after the ramp time (RT) 130 and where the set temperature (STp) 120 is reached about 5 seconds later at time 150. In this embodiment, the total procedure extension time is calculated to be about 5 seconds (the time between the ramp time and the time at which the threshold level was reached) plus about 5*0.5=1.25 seconds (i.e. 50% of the time at which the temperature was at the threshold level prior to reaching the set temperature), for a total procedure extension time of about 7.5 seconds.

In further embodiments, one or more tolerance levels may be defined within which the aforementioned procedure extension method may not be invoked. For example, if the temperature of one or more of the energy delivery devices is within, for example, about 5% or about 5° C. of the set temperature 120 at the romp time 130, the overall procedure time may not be extended. Alternatively or in addition, if the temperature of one or more of the energy delivery devices reaches the set temperature 120 within a specified time window, for example within about 3 seconds or 3% of the ramp time 130, the overall procedure time may not be extended. These tolerances may be pre-set by a user and/or may be adjustable by the user before or during a procedure, or may be adjustable automatically by the electrosurgical system depending, for example, on what energy delivery devices are coupled to the system.

In some situations, the pre-set parameter threshold or limit, for example the set temperature, may be reached substantially prior to the ramp time. In such cases, the electrosurgical system may be operable to reduce the overall procedure time by a time period responsive to, for example substantially equivalent to, the difference between when the parameter limit was reached and the ramp time, as is illustrated in the flow chart of FIG. 2A.

Figure 2B:
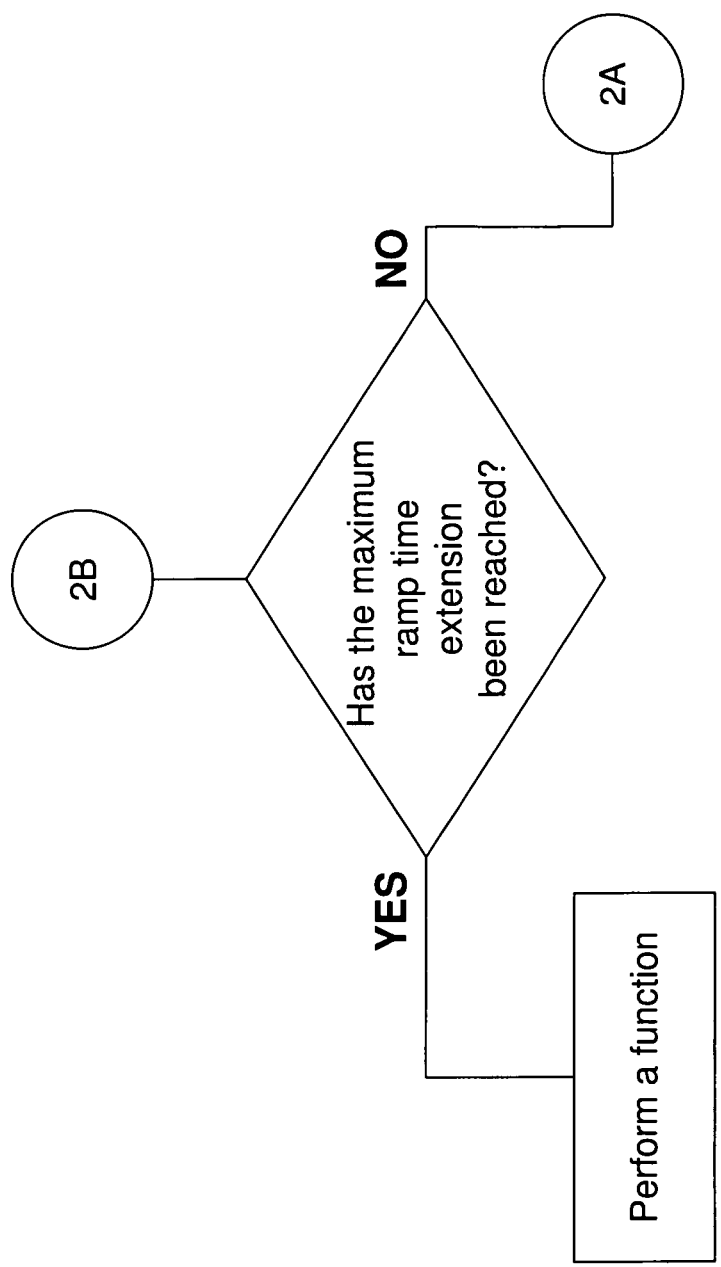

Furthermore, in some embodiments, a pre-set maximum ramp time extension may be defined for a given treatment procedure. This maximum ramp time extension, when added to the pre-set ramp time 130, defines a time period within which a parameter, for example the temperature associated with one or more energy delivery devices, must reach the pre-set threshold or limit, for example the set temperature 120. As illustrated in FIG. 2B, if the pre-set threshold or limit is not reached within this time, the generator performs a function, including but not limited to, alerting the user and/or modifying the treatment procedure, for example by stopping the delivery of energy or by modifying the algorithm by which the energy is delivered, for example in an application involving a plurality of energy delivery devices. Defining a maximum ramp time extension helps to ensure that the overall procedure time is not excessive. For example, rather than waiting for an extended amount of time for the temperature to reach the set temperature without alerting the user, the user may instead be alerted that the procedure time may be extended so that the user may determine whether or not to continue with the procedure. Alternatively, the generator may automatically stop the procedure in such a situation. The maximum ramp time extension may be adjustable and may be pre-set by the user. In some particular embodiments, the maximum ramp time extension may be between about 5 and about 120 seconds.

Thus, this aspect of the present invention provides a means for intra-procedurally assessing the likelihood of the success or failure of a treatment procedure. In other words, if the temperature, for example, has not reached the set temperature by the allotted time (e.g. the ramp time plus the maximum ramp extension time), it may be indicative of the failure of the procedure, and the user may be alerted to this possibility. In alternate embodiments, other parameters may be used to assess the likelihood of success or failure of the treatment procedure. For example, rather than assessing the temperature relative to the procedure timing, temperature may be assessed relative to the power delivered by the generator. In such an embodiment, if the temperature has not yet reached the set temperature but the power is no longer increasing, that may be indicative of the failure of the procedure, since the temperature is unlikely to increase without an increase in power.

For example, an electrosurgical generator may have a pre-set power limit corresponding to the maximum power deliverable by the generator. If this power limit is reached prior to the temperature reaching the set temperature, then the procedure is likely to fail, since no further increases of power are available to increase the temperature of the tissue, assuming that there are no other parameters that may be adjusted to increase the energy delivered to the tissue. For example, in an application wherein the electrosurgical system comprises a plurality of energy delivery devices and wherein energy is delivered to the energy delivery devices in accordance with a duty cycle, it may be possible to increase the "ON" time of one or more energy delivery devices to increase the energy provided to those devices. In such situations, rather than terminating the treatment procedure and in accordance with an embodiment of the present invention, a user may be alerted to the fact that the power limit has been reached and that, therefore, the "ON" time of one or more energy delivery devices should be adjusted.

Embodiments of the method of the present invention may also include a step wherein one or more other treatment parameters, in addition to the overall procedure time, are modified, for example in response to a measured parameter, such as temperature or impedance for example. Such treatment parameters may include, but are not limited to: characteristics of the energy delivered (including frequency, voltage, current and power, for example), the number of energy delivery devices operatively coupled and capable of delivering energy, or the configuration of one or more energy delivery devices.

Thus, as described herein above, embodiments of the present invention comprise a method for delivering energy to a body of a human or animal during a treatment procedure using an electrosurgical generator, a pre-set overall procedure time being defined for the treatment procedure, a romp time being defined for a parameter to reach a pre-set threshold during the treatment procedure, the method comprising: measuring the parameter over time; and if the parameter has not substantially reached the pre-set threshold by the romp time, setting a procedure extension time responsive to the time difference between the ramp time and the time at which the pre-set threshold was reached, and extending the overall procedure time by the procedure extension time.

In addition, as described herein above, in some embodiments of the present invention a maximum romp time extension is defined for the treatment procedure within which the parameter should reach the pre-set threshold. In such embodiments, the method further comprises: if the parameter has not substantially reached the pre-set threshold by a time equivalent to a sum of the ramp time and the maximum ramp extension time, performing a function, such as stopping or terminating the delivery of energy and/or alerting a user.

Furthermore, in some embodiments, the method further comprises: if the parameter has substantially reached the pre-set threshold before the romp time, setting a procedure reduction time responsive to the time difference between the ramp time and the time at which the pre-set threshold was reached and reducing the expected overall procedure time by the procedure reduction time.

In some embodiments of the present invention, the invention may be embodied by a computer readable medium including computer-executable instructions for interfacing with an electrosurgical generator during a treatment procedure, the instructions operable to implement one or more of the various methods described hereinabove.

Thus, embodiments of the present invention overcome various deficiencies in the prior art by allowing for intra-procedural adjustment of certain treatment procedure parameters responsive to a correlation of a measured treatment parameter (e.g. temperature) with another treatment parameter (including, but not limited to time and power). In some embodiments, one or more treatment parameters are adjusted responsive to the correlation, while in other embodiments another function may be performed if the likelihood of success of the treatment procedure is determined to be low.

The embodiments of the invention described above are intended to be exemplary only.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for intra-procedurally assessing a likelihood of failure of a treatment procedure, the treatment procedure comprising delivering energy to a body of a human or animal using an electrosurgical generator, a treatment parameter being associated with the treatment procedure, the treatment parameter having a pre-set threshold associated with a successful treatment procedure, and a ramp time being defined for the treatment parameter to reach the pre-set threshold during the treatment procedure, the ramp time having a pre-set limit, the method comprising:

measuring the treatment parameter over time from a start of the delivering of energy and during a course of the treatment procedure; and during the course of the treatment procedure, determining whether or not the treatment parameter will reach the pre-set threshold such that the treatment procedure is likely to be successful, by correlating the measured treatment parameter with the ramp time;

whereby a likelihood the treatment procedure will fail may be determined if the treatment parameter does not reach the pre-set threshold prior to the ramp time reaching the pre-set limit; and after the delivering of the energy for the ramp time has ended, adjusting an overall procedure time when the treatment parameter does not reach the pre-set threshold prior to the ramp time.

2. The method of claim 1, further comprising performing a function in response to the determining step if the treatment procedure is likely to fail.

3. The method of claim 2, wherein the function is selected from the group consisting of stopping the delivery of energy, alerting a user and a combination thereof.

4. The method of claim 1, wherein the correlation is performed when the ramp time has reached the pre-set limit.

5. The method of claim 1, wherein the treatment parameter comprises a temperature and wherein the pre-set limit comprises a maximum ramp time.

6. The method of claim 5, wherein correlating the temperature and the ramp time comprises assessing whether or not the temperature has substantially reached the preset threshold within the maximum ramp time.

* * * * *